US006248326B1

(12) United States Patent
Blair et al.

(10) Patent No.: US 6,248,326 B1
(45) Date of Patent: Jun. 19, 2001

(54) REGULATION OF OSTEOCLAST FORMATION BY INHIBITION OF OSTEOBLASTIC STEM CELL FACTOR

(76) Inventors: Harry C. Blair, 4459 Briar Glen Dr., Mountain Brook, AL (US) 35243; Sai-Sai Dong, 231 Loblolly Trace, Alpine, AL (US) 35014-7701; Bruce A. Julian, 1280 Parliament La., Vestavia Hills, AL (US) 35216

( * ) Notice: Subject to any disclaimer, the term of this patent is extended or adjusted under 35 U.S.C. 154(b) by 0 days.

(21) Appl. No.: 09/150,797

(22) Filed: Sep. 10, 1998

Related U.S. Application Data

(60) Provisional application No. 60/058,484, filed on Sep. 10, 1997, now abandoned.

(51) Int. Cl.[7] ..................... A61K 39/395; C07K 16/28; C07K 16/18
(52) U.S. Cl. ..................... 424/139.1; 424/130.1; 530/387.9; 530/388.7; 530/388.6
(58) Field of Search ............... 424/130.1, 131.1, 424/138.1, 139.1; 435/325, 327; 436/512, 547; 530/387.1, 387.2, 387.9, 388.15, 388.22, 388.24, 388.7, 389.6

(56) References Cited

U.S. PATENT DOCUMENTS 5,911,988 * 6/1999 Brownell et al. .

FOREIGN PATENT DOCUMENTS

91/05795 * 5/1991 (WO) .

OTHER PUBLICATIONS

Chatterjee et al, Idiotypic antibody immunotherapy of cancer, Cancer Immuno. Immunother. 38: 75–82. Jan. 1994.*
Osband et al, Problems in the investigational study and clinical use of cancer immuotherapy, Immunology Today 11(6): 193–195. Jun. 1990.*
Lemoli et al, Expression and functional role of c–kit ligand (SCF) in human multiple myeloma cells, Br. J. Haematology 88(4): 760–769. Apr. 13, 1994.*
Heidari et al, Characterization of the Growth Factor Activity of Amniotic Fluid on Cells from Hematopoietic and Lymphoid Organs of Different Life Stages, Microbiol. Immunol. 40(8):583–589. Aug. 23, 1996.*
Harlow et al, Antibodies: A Laboratory Manual, Cold Spring Harbor Laboratory, pp. 71–82. Dec. 1988.*
Dunham et al DNA Sequence vol. 6 233–237, 1996.*
Efferth et al Med Oncol Tumor Pharmacology vol. 9(1) 11–19, 1992.*
Blair et al J Bone Mineral Res vol. 12 Suppl 1 T380 p. S196, Aug. 1997.*
Seaver Genetic Engineering vol. 14 No. 14 pp. 10 and 21 Aug. 1994.*
Battei et al J Cellular Biochem Suppl vol. 0 No. 18 Part A p. 23 Abstract 300, 1994.* a. Eric J. Huang, et al. *Differential Expression and Processing of Two Cell Associated Forms of the Kit–Ligand: KL–1 and KL–2*, Molecular Biology of the Cell, vol. 3, pp. 349–362 (Mar. 1992).
b. Manas K. Majumdar, et al. *Identification and Mutation of Primary and Secondary Proteolytic Cleavage Sites in Murine Stem Cell Factor cDNA Yields Biologically Active, Cell–associated Protein*, The Journal of Biological Chemistry, vol. 269, No. 2, pp. 1237–1242 (Jan. 14, 1994).
c. Wayne E. Taylor, et al. *Human Stem Cell Factor Promoter Deoxyribonucleic Acid Sequence and Regulation by Cyclic 3', 5'–Adenosine Monophosphate in a Sertoli Cell Line*, Endocrinology, vol. 137, No. 12, pp. 5407–5414 (1996).
d. Krisztina M. Zsebo, et al. *Stem Cell Factor Is Encoded at the SI Locus of the Mouse and Is the Ligand for the c–kit Tyrosine Kinase Receptor*, Cell, vol. 63, pp. 213–224 (Oct. 5, 1990).
e. Dirk M. Anderson, et al. *Molecular Cloning of Mast Cell Growth Factor, a Hematopoietin that Is Active in Both Membrane Bound and Soluble Forms*, Cell, vol. 63, pp. 235–243 (Oct. 5, 1990).
f. Eric Huang, et al. *The Hematopoietic Growth Factor KL is Encoded by the SI Locus and Is the Ligand of the c–kit Receptor, the Gene Product of the W Locus*, Cell, vol., 63 pp. 225–233 (Oct. 5, 1990).
g. Francis H. Martin, et al. *Primary Structure and Functional Expression of Rat and Human Stem Cell Factor KNAs*, Cell, vol. 63, pp. 203–211 (Oct. 5, 1990).
h. Feihua Qiu, et al. *Primary Structure of c–kit: Relationship with the CSF–1/PDGF Receptor Kinase Family–Oncogenic Activation of v–kit Involves Deletion of Extracellular Domain and C Terminus*, The EMBO Journal, vol. 7, No. 4, pp. 1003–1011 (1988).
i. R.J. Van't Hof, et al. *Stem Cell Factor Stimulates Chicken Osteoclast Activity in vitro*, FASEB Journal, vol. 11, pp. 287–293 (1997).
j. Valter Gattei, et al. *Human Osteoclasts and Preosteoclast Cells (FLG 29.1) Express Functional c–kit Receptors and Interact with Osteoblast and Stromal Cells via Membrane–bound Stem Cell Factor*, Cell Growth and Differentiation, vol. 7, pp. 753–763 (Jun. 1996).

(List continued on next page.)

*Primary Examiner*—Anthony C. Caputa
*Assistant Examiner*—Anne L. Holleran
(74) *Attorney, Agent, or Firm*—Benjamin Aaron Adler

(57) ABSTRACT

The present invention provides an inhibitor of osteoblastic stem cell factor binding and/or activity, for example, an antibody or an antisense oligonucleotide. Also provided are pharmaceutical compositions comprising these inhibitors of osteoblastic stem cell factor binding and/or activity. Further provided is a method of regulating the activity of osteoclasts, comprising the step of: inhibiting the binding and/or activity of osteoblastic stem cell factor.

3 Claims, 19 Drawing Sheets

(5 of 19 Drawing Sheet(s) Filed in Color)

OTHER PUBLICATIONS k. L. Pierelli, et al. *Generation of Multinuclear Tartrate–resistant Acid Phosphatase Positive Osteoclasts in Liquid Culture of Purified Human Peripheral Blood CD34 +Progenitors,* British Journal of Haematology, vol. 96, No. 1, pp. 64–69 (Jan. 1997).

l. Y. Hayase, et al. *Osteoclast Development from Hematopoietic Stem Cells: Apparent Divergence of the Osteoclast Lineage Prior to macrophage Commitment,* Experimental Hematology, vol. 25, No. 1, pp. 10–25 (Jan. 1997).

m. S. Roux, et al. *Human Cord Blood Monocytes Undergo Terminal Osteoclast Differentiation in vitro in the Presence of Culture Medium Conditioned by Giant Cell tumor of Bone,* Journal of Cellular Phusiology, vol. 168, No. 3, pp. 489–498 (Sep. 1996).

n. S. Takahashi, et al. *Development and Characterization of a Human Marrow Stromal Cell Line that Enhances Osteoclast–Like Cell–Like Formation,* Endocrinology, vol. 136, No. 4, pp. 1441–1449 (Apr. 1995).

* cited by examiner

| | | |
|---|---|---|
| Bovine | EEDNEISMLQEKEREFQEV | (SEQ ID No. 5) |
| Feline | EEDNEISMLQEKEREFQEV | (SEQ ID No. 5) |
| Avian (Chicken) soluble | QEENEISMLQQKEKEHLEV | (SEQ ID No. 6) |
| Avian (Chicken) membrane | QEENEISMLQQKEKEHLEV | (SEQ ID No. 6) |
| Avian (Coturnix) | QEENEISMLQQKEKEHLEV | (SEQ ID No. 6) |
| Canine | EEDNEISMLQEKEREFQEV | (SEQ ID No. 5) |
| Human | EEDNEISMLQEKEREFQEV | (SEQ ID No. 5) |
| Human (short form) | EEDNEISMLQQKEREFQEV | (SEQ ID No. 5) |
| Murine | EEDNEISMLQQKEREFQEV | (SEQ ID No. 7) |
| O aries secreted | ------------------- | |
| Rat partial form | ------------------- | |
| Porcine | EEDNEISMLQEKEREFQEV | (SEQ ID No. 5) |

FIGURE 7

SEQUENCE LISTING

```
<160> NUMBER OF SEQ ID NOS: 7

<210> SEQ ID NO 1
<211> LENGTH: 10
<212> TYPE: PRT
<213> ORGANISM: Homo sapiens
<220> FEATURE:
<221> NAME/KEY:
<223> OTHER INFORMATION:

<400> SEQUENCE: 1

Glu Glu Asp Asn Glu Ile Ser Met Leu Gln
1               5                   10

<210> SEQ ID NO 2
<211> LENGTH: 21
<212> TYPE: DNA
<213> ORGANISM: artificial sequence
<220> FEATURE:
<221> NAME/KEY: primer_bind
<222> LOCATION:
<223> OTHER INFORMATION: synthesized

<400> SEQUENCE: 2
gcctttcctt atgaagaaga c                                      21
```

```
<210> SEQ ID NO 3
<211> LENGTH: 19
<212> TYPE: DNA
<213> ORGANISM: artificial sequence
<220> FEATURE:
<221> NAME/KEY: primer_bind
<222> LOCATION:
<223> OTHER INFORMATION: synthesized

<400> SEQUENCE: 3
tgctgtcatt cctaaggga                                                  19

<210> SEQ ID NO 4
<211> LENGTH: 21
<212> TYPE: DNA
<213> ORGANISM: artificial sequence
<220> FEATURE:
<221> NAME/KEY: primer_bind
<222> LOCATION:
<223> OTHER INFORMATION: synthesized

<400> SEQUENCE: 4
cggaaaggaa tacttcttct g                                               21

<210> SEQ ID NO 5
<211> LENGTH: 19
<212> TYPE: PRT
<213> ORGANISM: Homo sapiens
<220> FEATURE:
<221> NAME/KEY:
<223> OTHER INFORMATION:

<400> SEQUENCE: 5

Glu Glu Asp Asn Glu Ile Ser Met Leu Gln Glu Lys Glu Arg Glu
1               5                   10                  15

Phe Gln Glu Val

<210> SEQ ID NO 6
<211> LENGTH: 19
<212> TYPE: PRT
<213> ORGANISM: Gallus gallus
<220> FEATURE:
<221> NAME/KEY:
<223> OTHER INFORMATION:

<400> SEQUENCE: 6

Gln Glu Glu Asn Glu Ile Ser Met Leu Gln Gln Lys Glu Lys Glu
1               5                   10                  15

His Gln Glu Val

<210> SEQ ID NO 7
<211> LENGTH: 19
<212> TYPE: PRT
<213> ORGANISM: Mus musculus
<220> FEATURE:
<221> NAME/KEY:
<223> OTHER INFORMATION:

<400> SEQUENCE: 7

Glu Glu Asp Asn Glu Ile Ser Met Leu Gln Gln Lys Glu Arg Glu
1               5                   10                  15

Phe Gln Glu Val
```

REGULATION OF OSTEOCLAST FORMATION BY INHIBITION OF OSTEOBLASTIC STEM CELL FACTOR

CROSS-REFERENCE TO RELATED APPLICATION

This application claims benefit of provisional application Ser. No. 60/058,484, filed Sep. 10, 1997, now abandoned.

FEDERAL FUNDING LEGEND

This invention was created in part using funds from National Institutes of Health grant number AG12951. The federal government, therefore, has certain rights in this invention.

BACKGROUND OF THE INVENTION

1. Field of the Invention

The present invention relates generally to the fields of biochemical endocrinology and regulation of bone formation and degradation. More specifically, the present invention relates to regulation of osteoclast formation by inhibition of osteoblastic stem cell factor.

2. Description of the Related Art

The human skeleton is continuously remodeled, normally turning over in ~2 years and allows use of skeletal mineral in calcium homeostasis. The strength and shape of the skeleton is preserved by segmental replacement: a bone section is degraded by osteoclasts, formed from monocyte-macrophage precursors,[1-2] while osteoblasts, derived from stromal cells,[3] synthesize new bone. These unrelated cells differentiate in a coupled manner, producing a new bone section in a few weeks.

Overall bone turnover responds to parathyroid hormone, but how differentiation of osteoblasts and osteoclasts is coordinated locally to maintain bone integrity is poorly understood. Osteoclast differentiation requires that precursors contact osteoblast-like cells,[4] suggesting specialized recognition molecules. In situ unlabeled antibody and Western blot analysis revealed that osteoblasts express a surface-bound form of stem cell factor (SCF; c-kit ligand) during bone synthesis only. Stem cell factor production in isolated osteoblasts responds to parathyroid hormone. Differentiation of osteoclasts from monocytes is supported by osteoblast-derived stem cell factor-producing cells in vitro, a process interrupted by antibody or antisense oligonucleotide targeting stem cell factor, indicating that it is a key element controlling this process.

The SCF/kit signaling pathway is very complex. Briefly summarized, stem cell factor binding induces receptor dimerization, which is associated with phosphorylation. Activity is transduced through intracellular kinases of the src family, the oncogene c-Cbl and pI-3 kinase. Src and Cbl are required for osteoclast differentiation; src, Cbl and PI-3-kinase interact with other osteoclast signaling molecules.

When ionized calcium is suppressed, such as with retention of phosphate in kidney failure, parathyroid hormone is secreted in large quantities and bone turnover increases as much as ten-fold, coupling of bone formation and degradation is maintained. Occurrence of stem cell factor in bone of hyperparathyroid subjects was examined because abnormal mast cell differentiation occurs around bone trabeculae of these patients,[5] and this protein causes mast cell differentiation in vitro.[6] Stem cell factor is expressed in a variety of forms in several tissues,[7] with a soluble form produced by a six-exon transcript and a longer membrane-associated form produced by an eight-exon transcript.[8] Additional variation occurs with proteolytic cleavage and glycosylation.

The prior art is deficient in the lack of effective means of inhibiting osteoclast formation and activity and thereby regulating bone formation and/or degradation. The present invention fulfills this longstanding need and desire in the art.

SUMMARY OF THE INVENTION

The present invention discloses, inter alia, that an antibody to a conserved region of the C-terminus of the c-kit ligand completely blocks the formation of human osteoclasts. This region is present in membrane-bound and some secreted forms of the protein, but is absent from other reported forms of the protein and may not required for some functions of c-kit ligand. Furthermore, in a controlled in vitro system with only osteoblast-like stromal cells and monocytes, osteoclast formation is blocked by antisense nucleotides or antibodies to stem cell factor and thus is a unique limiting factor coupling bone cell differentiation.

Osteoclasts mediate bone degradation that is responsible for osteoporosis, bone lesions in metastatic cancer, and other disease states. Thus, an application of the present invention is to control osteoclast formation, and therefore bone loss, in disease states of bone loss.

Using a c-kit ligand to reduce bone degradation has the particular advantage of inhibiting a system that affects, in (receptor) deficient mi/mi mice, only mast cells, and therefore has limited or no toxicity. Further, use of C-terminal blocking to inhibit osteoclast activity uses a portion of the molecule with no other known function.

Thus, use of antibodies or antisense nucleotides specific for the c-kit ligand, can reduce or prevent bone loss in aging (osteoporosis) or cancer progression (metastatic bone disease). These compounds target both the formation (tartrate-resistant acid phosphatase-positive cells) and the activity (bone resorption) of osteoclasts.

In one embodiment of the present invention, there is provided an inhibitor of osteoblastic SCF binding and/or activity.

In another embodiment of the present invention, there is provided a pharmaceutical composition, comprising an inhibitor of osteoblastic stem cell factor binding and/or activity and a pharmaceutically acceptable carrier.

In yet another embodiment of the present invention, there is provided a method of regulating the activity of osteoclasts, comprising the step of: inhibiting the binding and/or activity of osteoblastic stem cell factor.

In still yet another embodiment of the present invention, there is provided a method of treating a pathophysiological state in an animal in need of such treatment, wherein the pathophysiological state involves bone loss, comprising the steps of: administering a pharmaceutical composition disclosed herein to the animal.

In another embodiment of the present invention, there is provided a method of diagnosing bone disorders, comprising the step of measuring the activity of osteoblastic stem cell factor.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows the effect of blocking stem cell factor on osteoclast production. FIG. 3A shows the human macrophages in 2 $cm^2$ tissue culture wells incubated 14 days with 0.5 $\mu$g/ml recombinant CSF-1 (Genzyme, Cambridge, Mass.) added at 3 day increments (required for cell viability in absence of stromal cells). TRAP, a characteristic product of osteoclast differentiation, is not present, although many giant cells have formed. FIG. 3B shows the macrophages as in FIG. 3A co-cultured 14 days with MG63 cells (passage 43, $10^4$ per $cm^2$ at day 0 and near-confluent at day 14). In this control culture, pre-immune rabbit serum at 1:100 dilution was added to control for the rabbit serum addition in FIG. 3D below. Note that the giant cells formed are strongly TRAP positive (red color). FIGS. 3C–3D shows the anti-stem cell factor antibody at 1:500 and 1:100 dilution respectively, with dose-dependent decrement in staining. Bars: 20 $\mu$m.

FIG. 6 illustrates MG63 cells stably transfected with pCDNA3 containing antisense to the translation start site of human c-fms ligand driven by the CMV promoter.

FIG. 7 shows a comparison of the C-terminal sequences (with region for antibody production boxed) of several proteins.

DETAILED DESCRIPTION OF THE INVENTION

Figure 1A:
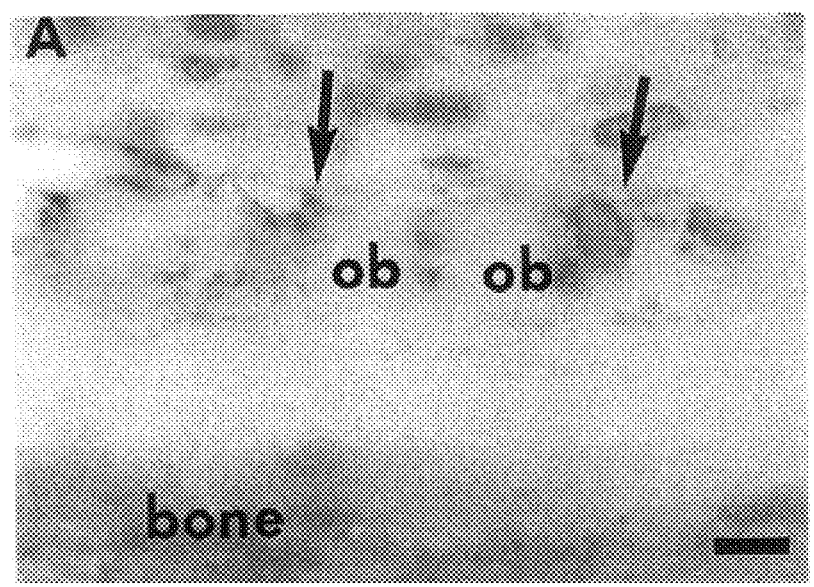
FIGS. 1A–1D shows stem cell factor in bone biopsy sections. Seven $\mu$m sections of formalin fixed, methacrylate embedded tissue were de-plasticized and stem cell factor was identified by the unlabeled antibody technique, with hematoxylin counter-stain to show cellular detail. Stem cell factor in single sections from hyperparathyroid (FIGS. 1A, 1D) and normal (FIGS. 1C, 1D) patients demonstrate reaction (brown color) of the antibody with cuboidal active osteoblasts (ob) (FIGS. 1A and 1C) in a membrane pattern (arrows). Quiescent, attenuated osteoblasts (FIGS. 1B and 1D) were nonreactive. Irrelevant hybridoma supernatant was nonreactive (not illustrated). Scale bars, 5 $\mu$m.

The present invention provides an inhibitor of osteoblastic SCF binding and/or activity. In one aspect, the inhibitor is an antibody. Preferably, the inhibitor is directed against the membrane associated form of osteoblastic SCF and the antibody is directed against the C-terminal end of the SCF protein. In a preferred embodiment, the antibody is directed against the C-terminal end comprises the decapeptide, EED-NEISMLQ (SEQ ID No.:1). Both human and non-human forms of the antibody can be employed for the various uses described herein. In another aspect, the present invention relates to an antisense oligonucleotide directed against expression of the stem-cell factor. Preferably, the antisense oligonucleotide is directed against the stem-cell factor transcription start site.

In another aspect, the present invention relates to a method of regulating the activity of osteoclasts, comprising the step of: inhibiting the binding and/or activity of osteoblastic stem cell factor. Both the antibodies and the antisense oligonucleotides described above are useful in this method.

It is specifically contemplated that pharmaceutical compositions may be prepared using the antibodies and the antisense oligonucleotides of the present invention. In such a case, the pharmaceutical composition comprises the antibodies and the antisense oligonucleotides of the present invention and a pharmaceutically acceptable carrier. A person having ordinary skill in this art would readily be able to determine, without undue experimentation, the appropriate dosages and routes of administration of the antibodies and the antisense oligonucleotides of the present invention.

In therapeutic applications, the oligonucleotides are utilized in a manner appropriate for treatment of a variety of conditions by inhibiting expression of the target genetic regions. For such therapy, the oligonucleotides alone or in combination can be formulated for a variety of modes of administration, including systemic, topical or localized administration. Techniques and formulations generally can be found in *Remington's Pharmaceutical Sciences*, Mack Publishing Co., Easton, Pa. The oligonucleotide active ingredient is generally combined with a pharmaceutically acceptable carrier such as a diluent or excipient which can include fillers, extenders, binders, wetting agents, disintergrants, surface active agents or lubricants, depending on the nature of the mode of administration and dosage forms. Typical dosage forms include tablets, powders, liquid preparations including suspensions, emulsions, and solutions, granules, capsules and suppositories, as well as liquid preparations for injections, including liposome preparations.

For systemic administration, injection is preferred, including intramuscular, intravenous, intraperitoneal and subcutaneous. For injection, the oligonucleotides of the invention are formulated in liquid solutions, preferably in physiologically compatible buffers. In addition, the oligonucleotides can be formulated in solid form and redissolved or suspended immediately prior to use. Lyophilized forms are also included. Dosages that can be used for systemic administration preferably range from about 0.01 mg/kg to 50 mg/kg administered once or twice per day. However, different dosing schedules can be utilized depending on: (1) the potency of an individual oligonucleotide at inhibiting the activity of its target DNA; (2) the severity or extent of the pathological disease state; or (3) the pharmacokinetic behavior of a given oligonucleotide.

In another aspect, the present invention relates to a method of treating a pathophysiological state in an animal in need of such treatment. A representative pathophysiological state would be one that involves bone loss. This method comprises the steps of: administering a pharmaceutical composition disclosed herein to said animal. Preferably, the pathophysiological state is selected from the group consisting of osteoporosis, bone cancer and malignant hypercalcemia.

In another aspect, the present invention relates to a method of diagnosing bone disorders state in an individual, comprising the step of measuring the activity of osteoblastic stem cell factor in a sample taken from said individual. Representative bone disorders which can be diagnosed using this technique include osteoporosis, hyperparathyroidism, metastatic cancer and hypercalcemia.

In one embodiment of the present invention, a diagnostic use of stem cell factor assays can be employed for the diagnosis of bone disorders. This assay is an inexpensive serum-based test.

A person having ordinary skill in this art would also recognize that the immuno-therapeutic potential of an antibody to block stem cell factor activity. Such immunotherapy could be useful for malignant hypercalcemia where short term control is important and may be much less toxic than what is used now, e.g., (1) gallium nitrate, (2) a large number of bisphosphonate derivatives, (3) antibiotics inhibitors herbimycin and plicamycin (plicamycin is also known as mithramycin, and has been abandoned due to severe toxicity), (4) bone-binding antibiotics, principally tetracyclines, (5) proteinase inhibitors, (6) estrogen analogues or inhibitors (raloxifene, tamoxifen), and (6) tyrosine kinase inhibitors (genistein, herbimycin).

Another aspect of the present invention involves attacking normal stem cell factor ligand binding using peptide inhibitors. This could include recombinant stem cell factor (need not be human) with defects added to make a form that will bind to, but not activate, receptors. This peptide inhibitor would preferably be in the 300–500 kDa range. Alternatively, one may attack the system using low-molecular weight inhibitors that are either much smaller peptides or are non-peptide molecules. This approach would involve crystallizing the long form of SCF for detailed molecular analysis.

The following examples are given for the purpose of illustrating various embodiments of the invention and are not meant to limit the present invention in any fashion.

EXAMPLE 1

Development of Antibody to a Conserved Sequence of the c-kit Ligand

Figure 3A:
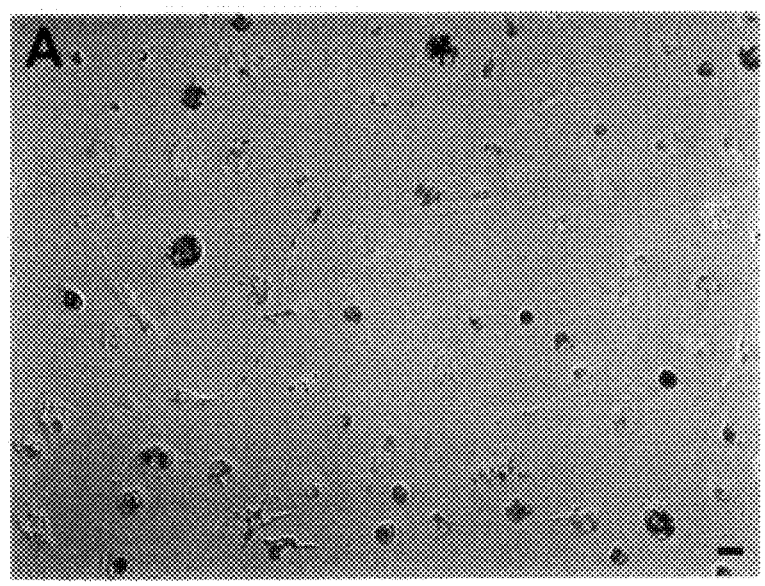
FIGS. 3A–D shows tartrate-resistant acid phosphatase (TRAP)-positive cells derived from macrophages cultured with MG63 cells and effect of antibody to stem cell factor.
Figure 3B:
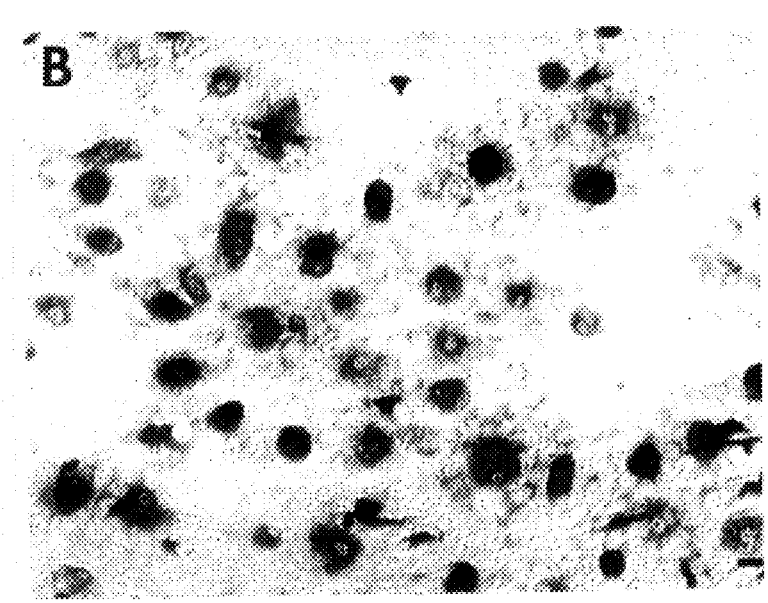
Figure 3C:
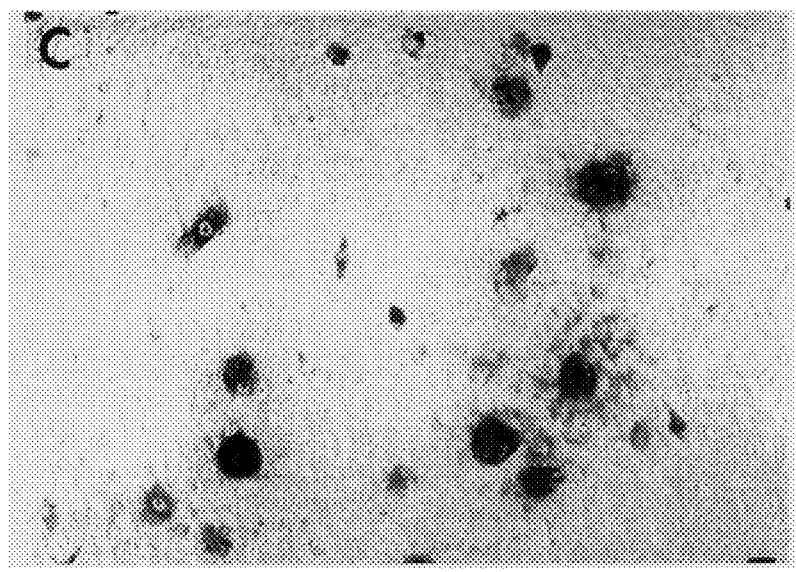
Figure 3D:
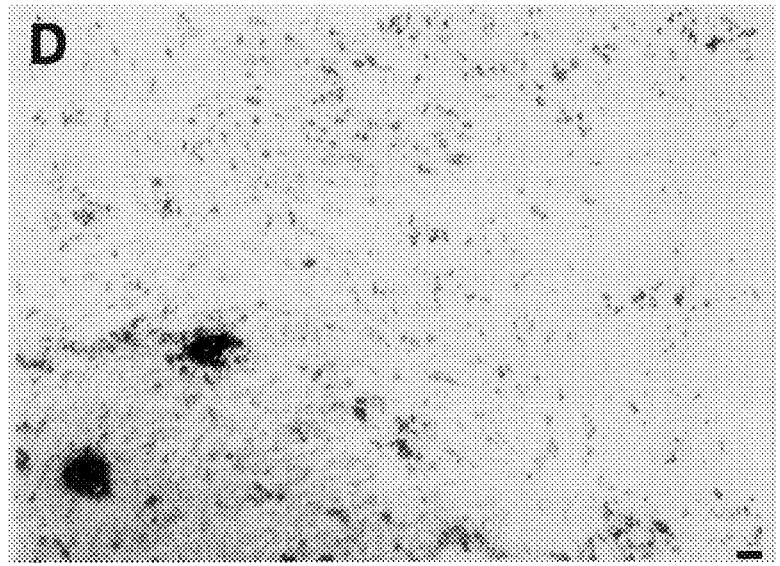
Figures 1, 3E:
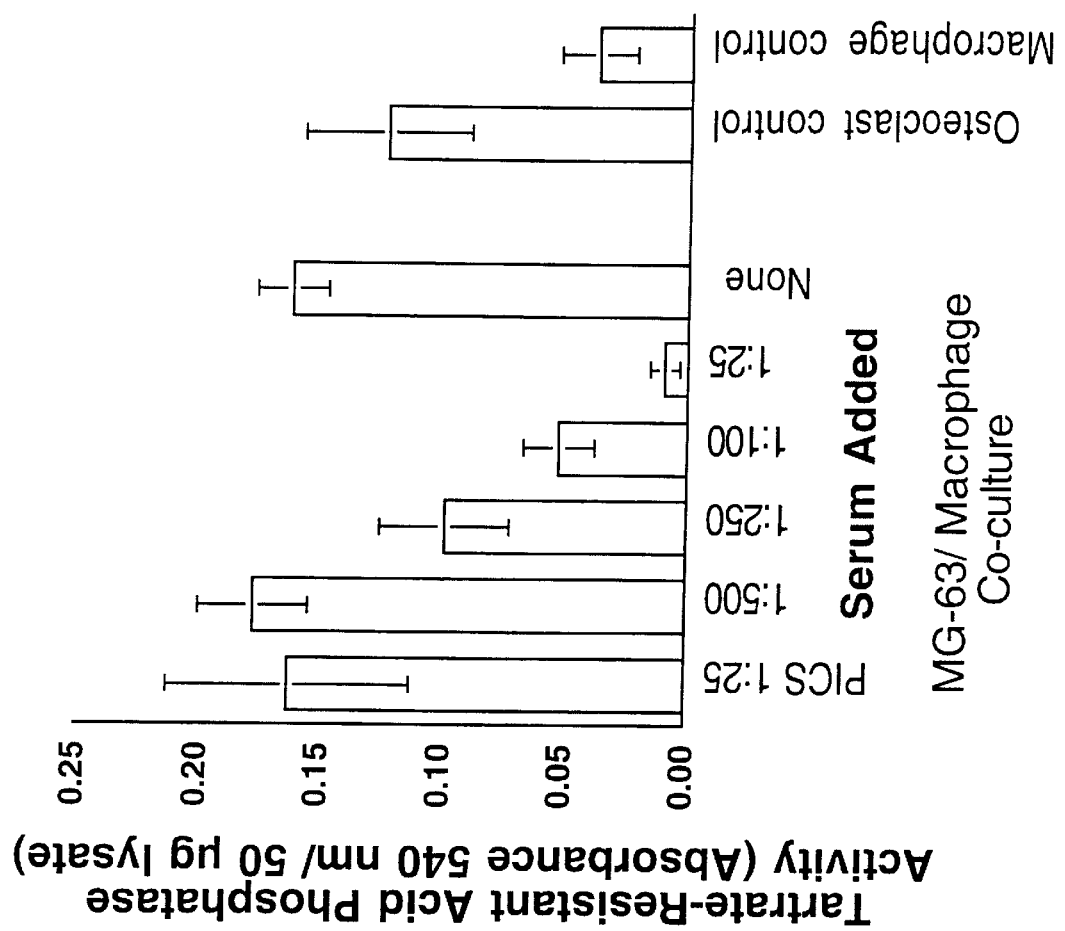
FIG. 1 shows the SCF production in human bone cells.
FIG. 3E shows the effect of stem cell factor antibody on TRAP activity in 14 days co-cultures of human macrophages with MG63 (left) or SaOS2 (right) cells. Pre-immune rabbit serum (1:25, PICS) control and a wide range of serum concentrations are tested using MG63 and SaOS2 cells to support osteoclast differentiation. Antibody (Ab) concentration-dependent reduction of TRAP occurs in both cases. Macrophage (10 $\mu$g, MF) and chicken osteoclast[21] lysates (2 $\mu$g, OC) are positive and negative controls.
Figures 2, 3E:
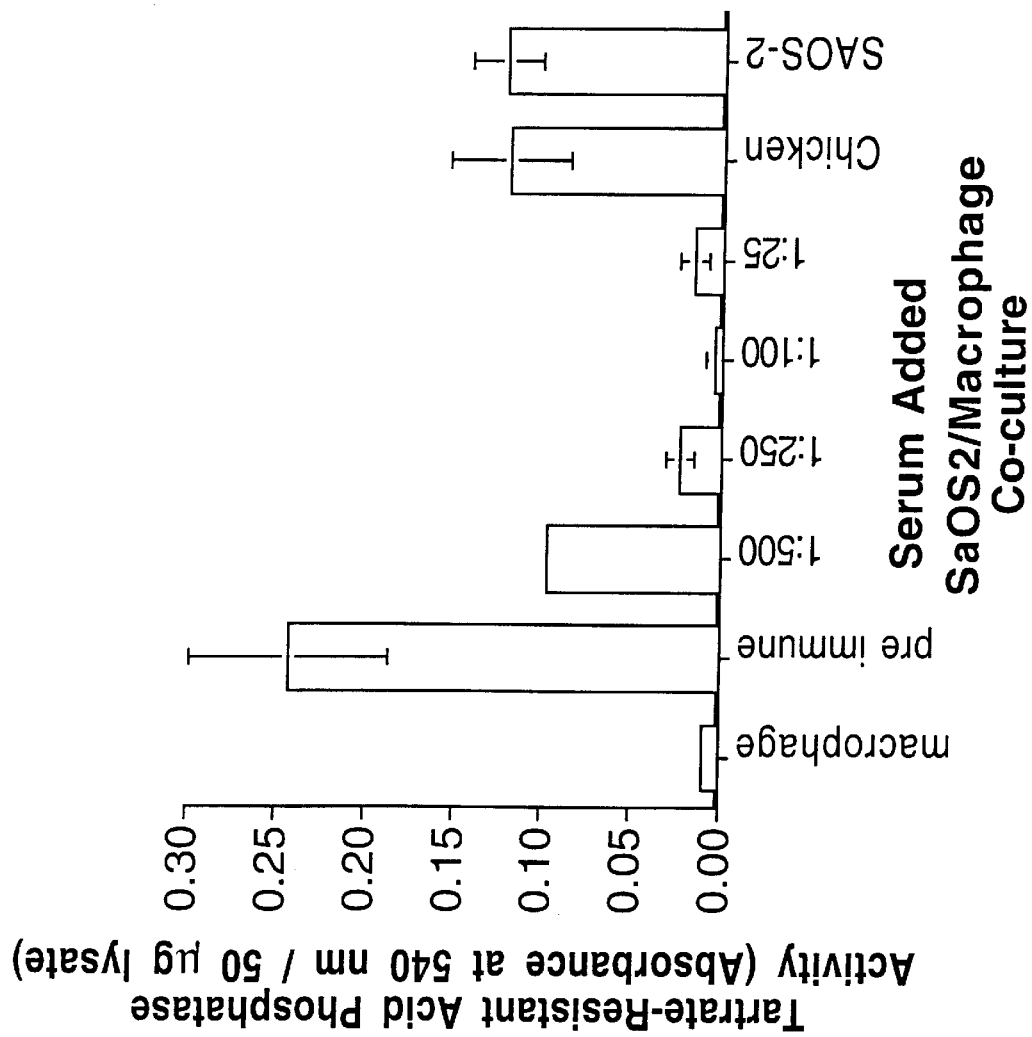
FIG. 2 shows the stem cell factor production by osteoblast-like cell lines and osteoblasts.

Monoclonal antibody 7H6 to human stem cell factor (Amgen, Thousand Oaks, Calif.) was used for FIG. 1. Western blot analysis[8] in FIG. 2 used rabbit polyclonal anti-human stem cell factor (Medical and Biological Laboratories, Nagoya, Japan).

The antibody to a hydrophilic, antigenic portion in the C-terminal stem cell factor was made in isolation from truncated (soluble) forms of the molecule.[8] The decapeptide, EEDNEISMLQ (SEQ ID No.:1), nine residues from the C-terminal of human stem cell factor, was synthesized as a multi-antigen peptide on a branched lysine core (Research Genetics, Huntsville, Ala.). Rabbit antibodies were generated using Freund's adjuvant; selected antiserum reacted in ELISA at 1:10,000 dilution, and recognized the $M_r$~45 kD form of SCF on Western blots. Antigen-inhibitable reaction with living MG63 cells showed that this epitope is exposed on these cells.

Amino-acid sequences of stem cell factors from dog (GenBank accession S53329), chicken (SC), human (M59964), Japanese quail (U43078, U43079) and mouse (M57647) were aligned by the clustal method. A hydrophilic, antigenic decapeptide, EEDNEISMLQ (SEQ ID No.:1), nine residues from the C-terminal end of the stem cell factors, was selected for antibody production. This region is identical in the five species except for E/Q or D/E substitutions in the avian species in its leading three acidic residues. It was chosen based on its position in the molecule, is present in both soluble- and membrane-forms of stem cell factor, and is the best conserved region with very high Kyte-Doolittle hydrophilicity score, Jameson-Wolf antigenic index, and Emini surface probability. Further, this region is centered in a beta amphipathic region with turns, a combination of features designed to select a surface region involved in protein-protein interactions. Analysis used Lasergene bio-computing software (DNASTAR, Madison, Wis.).

The selected region was synthesized as a multi-antigen peptide on a branched lysine core (Research Genetics, Huntsville, Ala.) and used with Freund's adjuvant with primary and two booster doses to generate antibodies in rabbits, with one selected for further use on the basis of enzyme-linked immune assay titers and Western analysis results.

EXAMPLE 2
Oligonucleotide Synthesis

A cDNA probe for stem cell factor mRNA was made by reverse transcription and polymerase chain reaction using RNA from MG63 cells and primers GCCTTTCCTTAT-GAAGAAGAC (SEQ ID No.:2) and TGCTGTCATTC-CTAAGGGA (SEQ ID No.:3) to produce a 633 bp segment from −10 to 633 relative to transcription start (GenBank M59964), product identity confirmed by restriction digestion. Sense and antisense phosphorothioate oligonucleotides were made using the first primer sequence and its complement (CGGAAAGGAATACTTCTTCTG) (SEQ ID NO.:4).

EXAMPLE 3
Northern Blot Analysis

For Northern analysis, RNAs were isolated by phenol-GITC extraction; 5 µg aliquots were separated on agarose and transferred to nitrocellulose for hybridization. The 633 bp segment of human stem cell factor cDNA, labeled with $^{32}$P by random priming, was denatured and hybridized to the blot at 42° C. overnight.[18] Membranes were washed in 300 mM NaCl, 50 mM Na citrate, pH 7.0 15 minutes at room temperature (25° C.), and twice in 30 mM NaCl, 5 mM Na citrate, pH 7.0, 15 minutes, 65° C., and autoradiographed.

EXAMPLE 4
Cell Culture and Enzyme Assays

Human macrophages were isolated by apheresis of volunteers, selecting surface-attached (1 hour), >99% non-specific esterase positive, cells.[19] Each assay used a single macrophage preparation. Human osteoblasts were produced from medullary bone from surgical waste,[20] grown to confluence in Eagle's minimal essential with 10% heat-inactivated fetal bovine serum and 1 µM cortisol, and used when mineralizing nodules appeared (~3 weeks). Mean ± standard deviation, n=4. TRAP was measured a s described.[21] Media were replaced at 3 day intervals except for antisense assays where they were replaced every 2 days. For quantitative assays, TRAP was determined as absorbance at 540 nm.

Figure 1B:
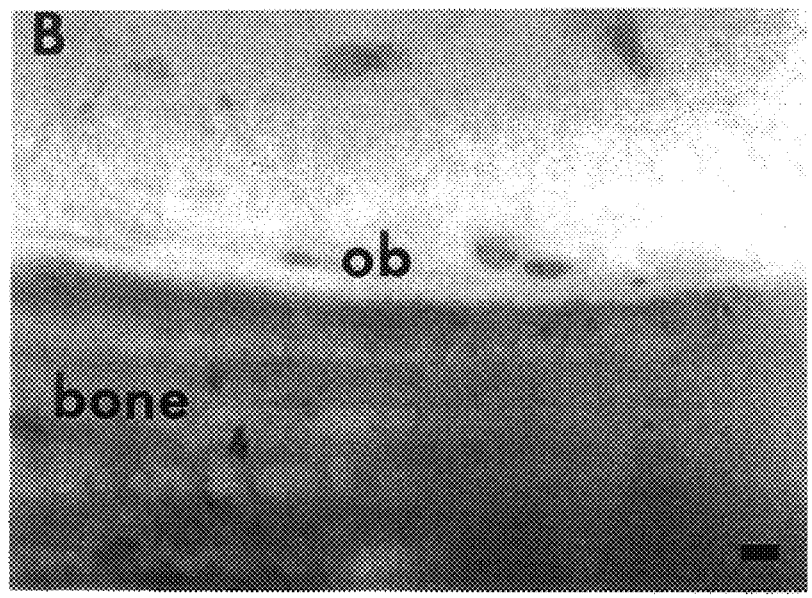
Figure 1C:
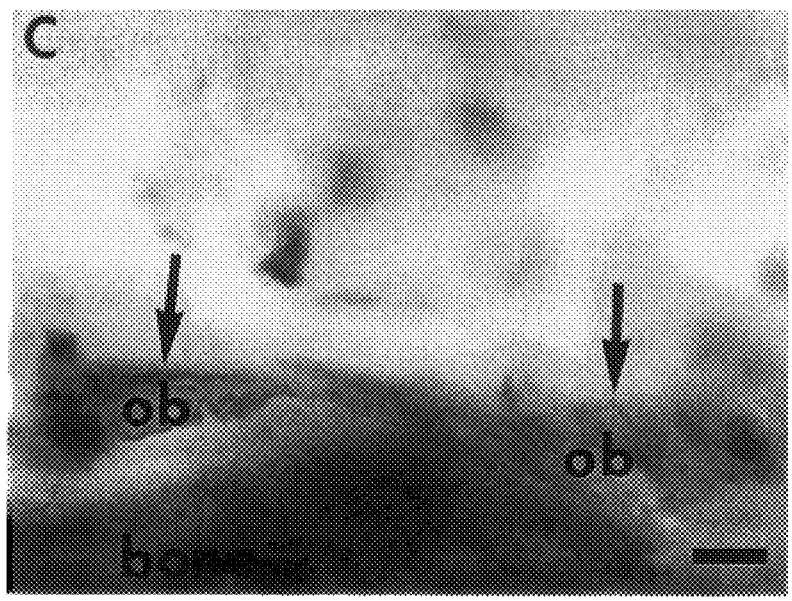
Figure 1D:
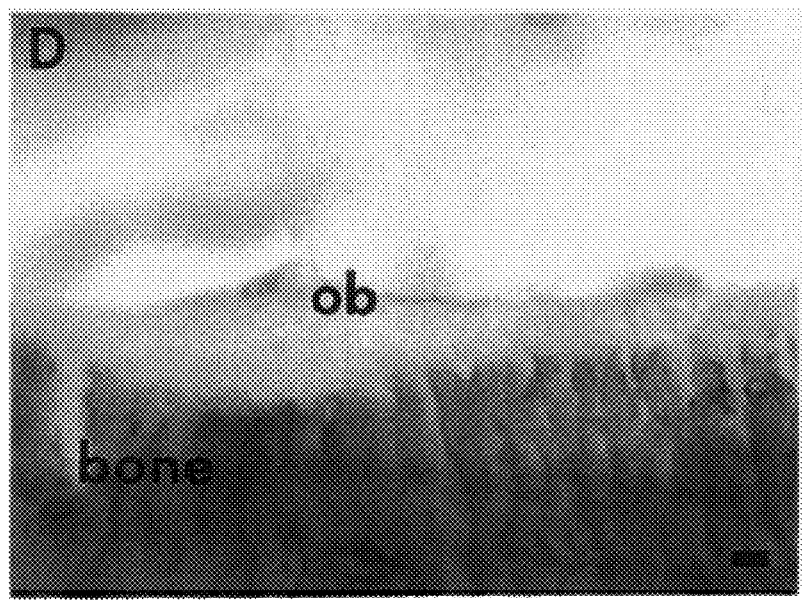

EXAMPLE 5
Stem Cell Factor Expression on the Surfaces of Synthetic Osteoblasts Stem cell factor was markedly expressed on the non-matrix surfaces of synthetic osteoblasts, but stem cell factor expression was not detected on quiescent osteoblasts (FIGS. 1A, 1B). Because the association with osteoblast activation suggested an important function for this cytokine, normal bone was also examined (FIGS. 1C, 1D). The pattern was the same, although active osteoblasts were, as expected, a much smaller proportion of the bone lining cells.

Figure 1E:
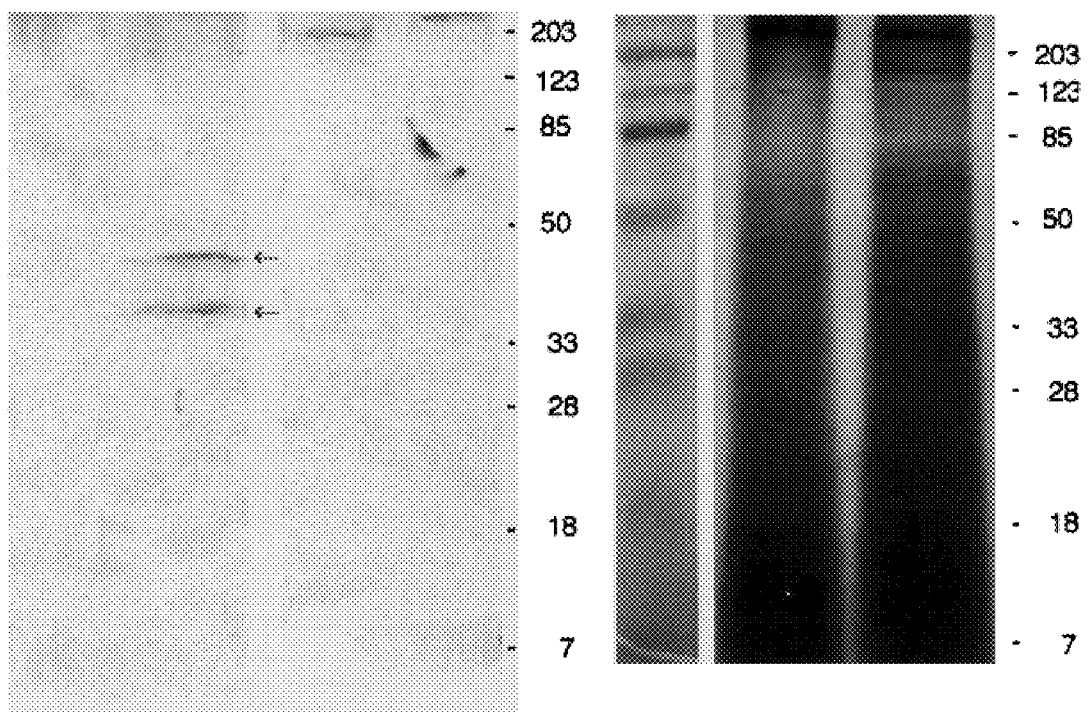
FIG. 1E shows a Western blot analysis of bone trabecular and marrow cells. Vertebral trabecular bone from patient with rapid bone loss (autopsy tissue from a 52 year old female on cortisol therapy) was separated from marrow by vortexing and 100 $\mu$g aliquots of protein separated on SDS-PAGE for Western blot analysis as described.[8] Non-reactive hybridoma supernatant and marrow cell protein were not labeled by the antibody, but bone cell proteins at $M_r$~45 and ~33 kD were labeled. Results are representative of several reactions.

Western blot analysis showed that stem cell factor associated with bone lining cells was predominately the large form, although smaller forms were also present (FIG. 1E). Production of stem cell factor production by bone-forming osteoblasts suggested that this factor is important in bone turnover. When turnover is amplified in hyperparathyroidism, formation of mast cells may occur as a side-effect.

The present invention shows that osteoblast surface stem cell factor plays a role in terminal differentiation of osteoclast precursors and this is the principal process linked to bone formation. It was known that pre-osteoclasts bear c-kit,[9] and osteoblast-like cells that support osteoclast differentiation in vitro produce stem cell factor.[10] Further, mi/mi mice, which have no mast cells and are osteopetrotic, have a defect in the W locus that produces c-kit.[11] Osteoblastic regulation of stem cell factor under controlled conditions was shown in vitro, using defined populations of human blood monocytes[2] and osteoblast-like stromal cellsl[2].

EXAMPLE 6
Production of SCF by Osteoblast-Like Cells

Figure 2A:
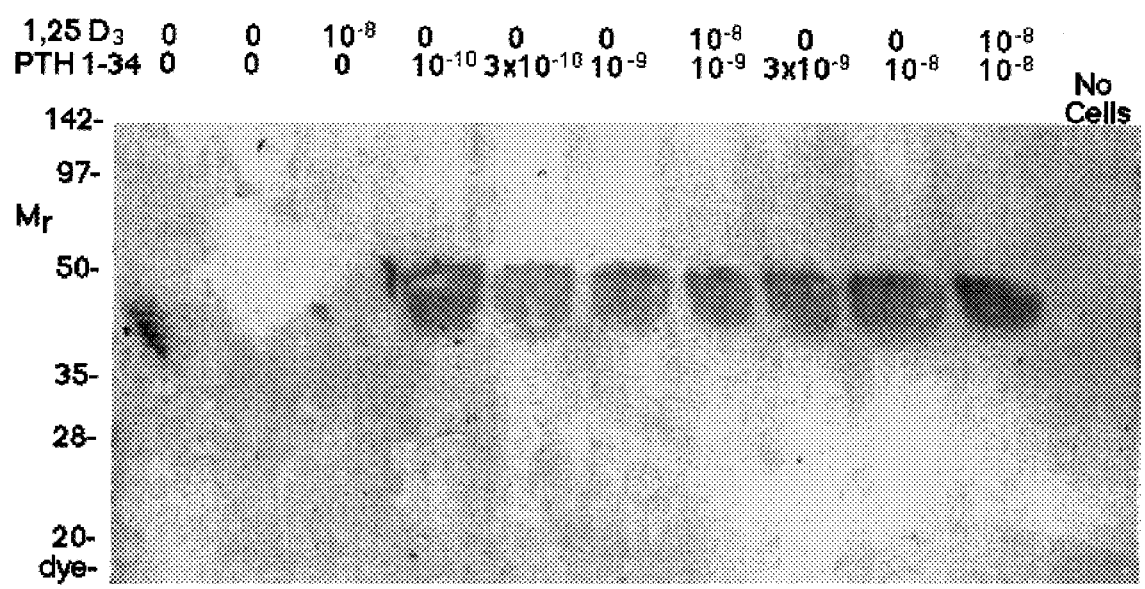
FIG. 2A shows a Western blot analysis of SaOS2 human osteosarcoma cells with indicated hormones during 5 day pre-treatment; stem cell factor production was very low unless parathyroid was present; 1,25-dihydroxyvitamin D had no effect. Unlike normal bone cells (see FIG. 1E), only one form, $M_r$~45 kD, was observed.
Figure 2B:
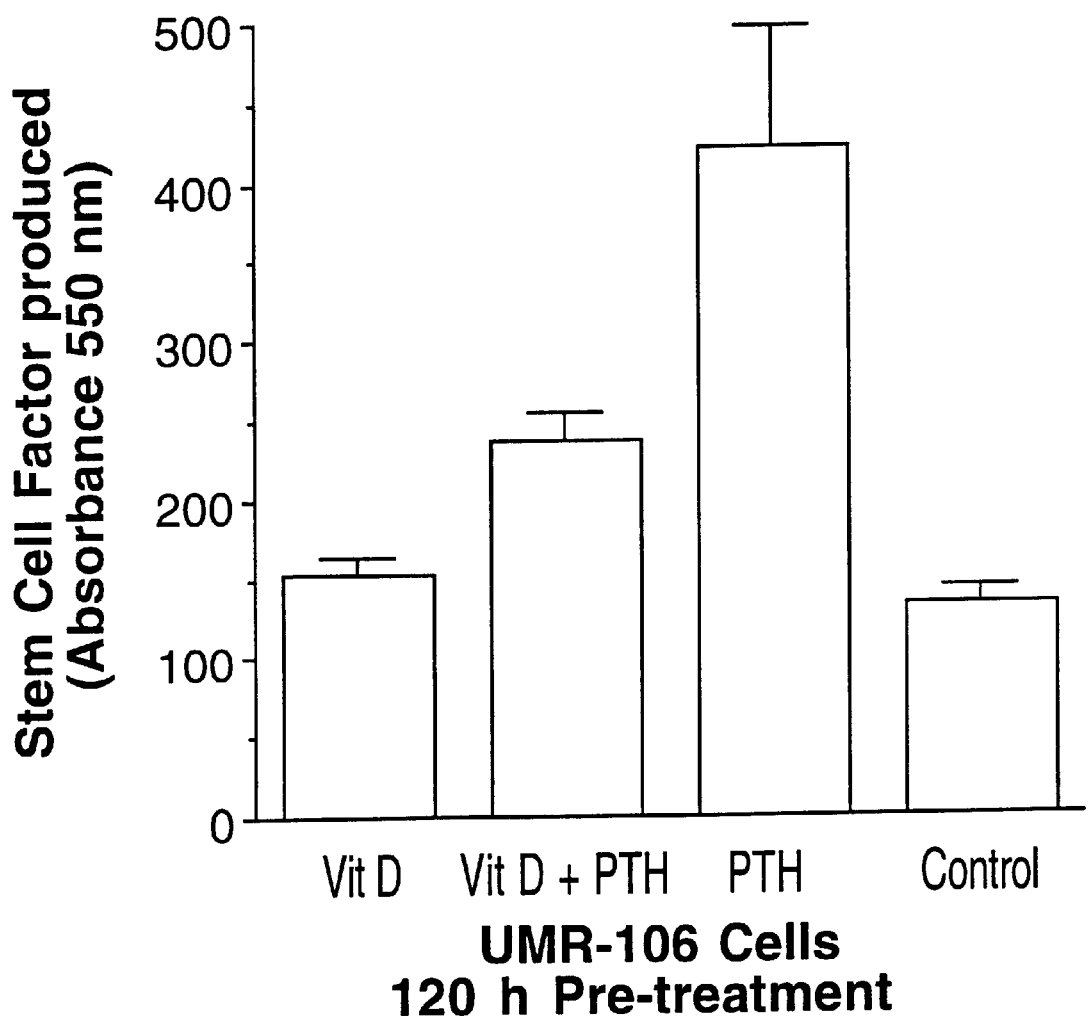
FIG. 2B shows an ELISA assay of UMR-106 cells. This rat osteoblast-like line, at passage 10, was treated for 120 hours with $10^{-9}$ M parathyroid hormone (PTH), $10^{-8}$ M 1,25-dihydroxyvitamin D (D), or both. For the ELISA assay, microtiter wells were coated with 5 $\mu$g of protein; bound human anti-stem cell factor was determined using alkaline phosphatase-coupled anti-rabbit serum (Bio-Rad, Richmond, Calif.) and p-nitrophenol-$PO_4$ substrate, with absorbance at 550 nm. Quadruplicate results ± standard deviation are shown in this and subsequent quantitative assays. Time course showed minimal parathyroid hormone effect at 1–3 days pre-incubation and Western analysis was similar to FIG. 1E (not illustrated).
Figure 2C:
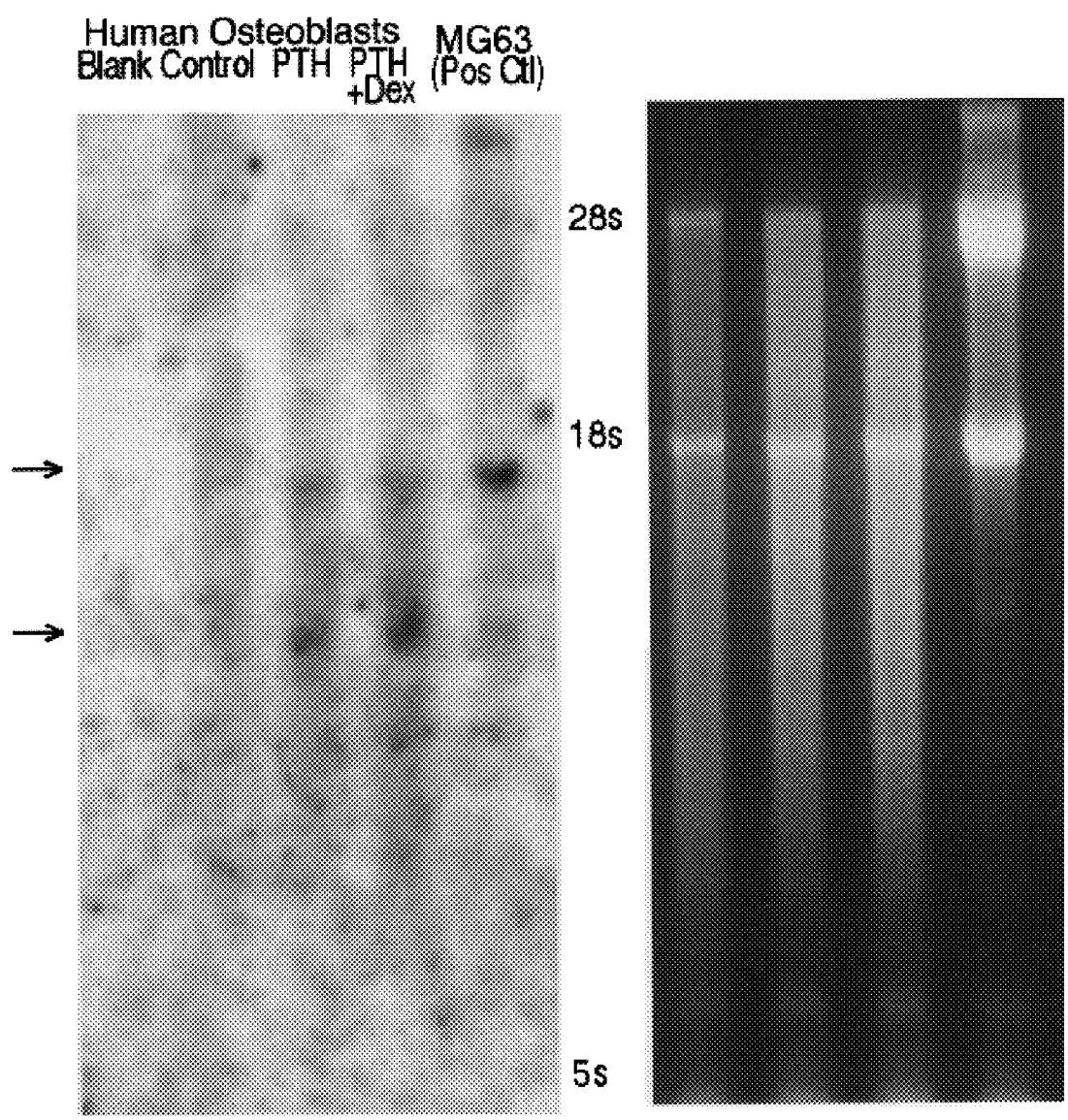
FIG. 2C shows a Northern blot analysis of stem cell factor in isolated human osteoblasts. Cells were pre-treated 120 hours in indicated conditions. Two mRNAs are detected, just as two sizes of the protein are present in non-transformed human osteoclasts (FIG. 1C). MG63 RNA is a positive control (right lane); osteoblasts produce barely detectable levels of mRNA (left lane) except when $10^{-9}$ M parathyroid hormone is added (second lane), a process unaffected by glucocorticoids (third lane).

To define the properties of the system, the production of stem cell factor by human and rat osteoblast-like cells in vitro was first determined. As seen in SaOS-2 human osteosarcoma cells, the production of stem cell factor was in some cases responsive to parathyroid hormone, but did not respond to 1,25 dihydroxyvitamin D, a steroid required for normal bone differentiation (FIG. 2A, 2B). Osteoclasts and osteoclast precursors did not produce detectable stem cell factor (not illustrated). Production of stem cell factor by nontransformed human osteoblasts in vitro, and parathyroid hormone activation, was also confirmed (FIG. 2C) to provide a more controlled demonstration of the findings in situ (FIG. 1).

ELISAs (FIG. 2B) of the rat osteoblast-like cell line, UMR-106, at passage 10, indicate that vitamin D has a negative effect on stem cell factor production. PTH, conversely, is seen to drive stem cell factor to high levels. For the ELISA, micro-titer wells were coated with 5 µg of target cell protein, and bound anti-human stem cell factor was determined, using alkaline phosphatase-coupled anti-rabbit serum (BioRad, Richmond, Calif.) and p-nitrophenol substrate, absorbance at 550 nm. Blank solutions of matched volumes were used as controls. These assays were run in quadruplicate in 96-well plates. These results indicate that stem cell factor production in osteoblast-like cell lines, including the non-human line UMR-106, is similar to normal osteoblasts, but with varying hormonal responses.

EXAMPLE 7
Immunofluorescent Detection of SCF in Live Cells

Figure 4:
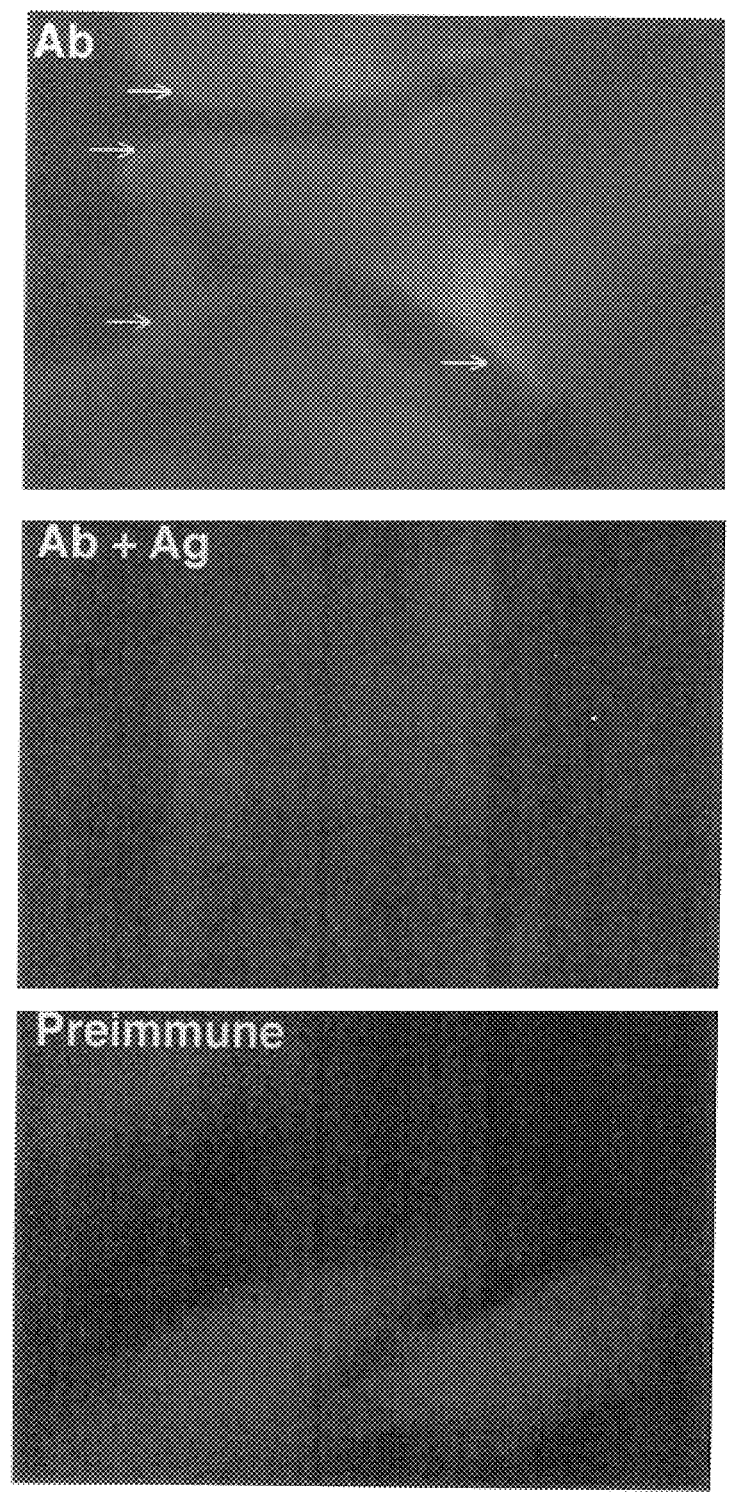
FIG. 4 demonstrates antibody staining in living MG63 cells. A patchy surface staining pattern is seen (arrows, left panel). The reaction can be successfully inhibited by pre-incubation of the antibody with excess antigen (middle panel). Incubation with pre-immune serum results in only faint background fluorescence.
Figure 5:
FIG. 5 depicts a Western blot analysis of stem cell factor production with sense/antisense treatment. In this figure, the form of stem cell factor at 45 kDa is seen clearly. Consistent inhibition was seen at time periods greater than five days following treatment with 1.5 $\mu$M antisense oligonucleotide.

For the staining observed on living MG63 cells (FIG. 4), cells were prepared as for Northern or Western analysis. They were then passed to 10 cm$^2$ wells in 6-well plates and grown on 25 mm coverslips. The protein localization via immunofluorescence used permeabilized fixed cells. The stem cell factor antibody was labeled with fluorescein. The anti-stem cell factor antibody is specific for SEQ ID No: 1. Antibody, antibody plus excess antigen, or preimmune serum at 1:100 were incubated for 30 minutes with living cells. The cells were then lightly fixed and bound antibody visualized with fluorescein-conjugated goat-anti-rabbit serum a s analyzed by epifluorescence microscopy. Fluorescent detection of stem cell factor in MG63 cells is shown in FIG. 4E.

EXAMPLE 8
Antibody Blockade of SCF

Osteoblast-like cells induce production of tartrate-resistant acid phosphatase (TRAP), an osteoclast marker, in fusing human monocytes in co-culture one week, which was blocked in a dose-dependent manner by addition of antibody to stem cell factor (FIGS. 3A–3D). The antibody used was directed at a conserved region of the protein (SEQ ID NO: 1) unique to the membrane associated form. Reaction of antibody with the surface of living MG-63 cells, which was blocked by pre-incubation of antibody with antigen, showed that this epitope is exposed in the cells studied (FIG. 4).

For these studies, one MG63 cell preparation and one macrophage preparation were used. Cultures were in 2 cm$^2$ cells on one 24 well plate, with 50 mg/cm devitalized bone. For the culture of macrophages without MG63 coculture, 0.5 µg/ml recombinant CSF-1 (Genzyme, Cambridge, Mass.) added at 3 day increments (required for cell viability in absence of stromal cells). The MG63 cells that were co-cultured with the macrophages were at passage number 43, with a cell density of 10$^4$ per cm$^2$ at day 0 and near-confluent at day 14. The antibody employed for stem cell factor detection was the decapeptide, EEDNEISMLQ (SEQ ID NO.: 1), as described supra.

Figure 3F:
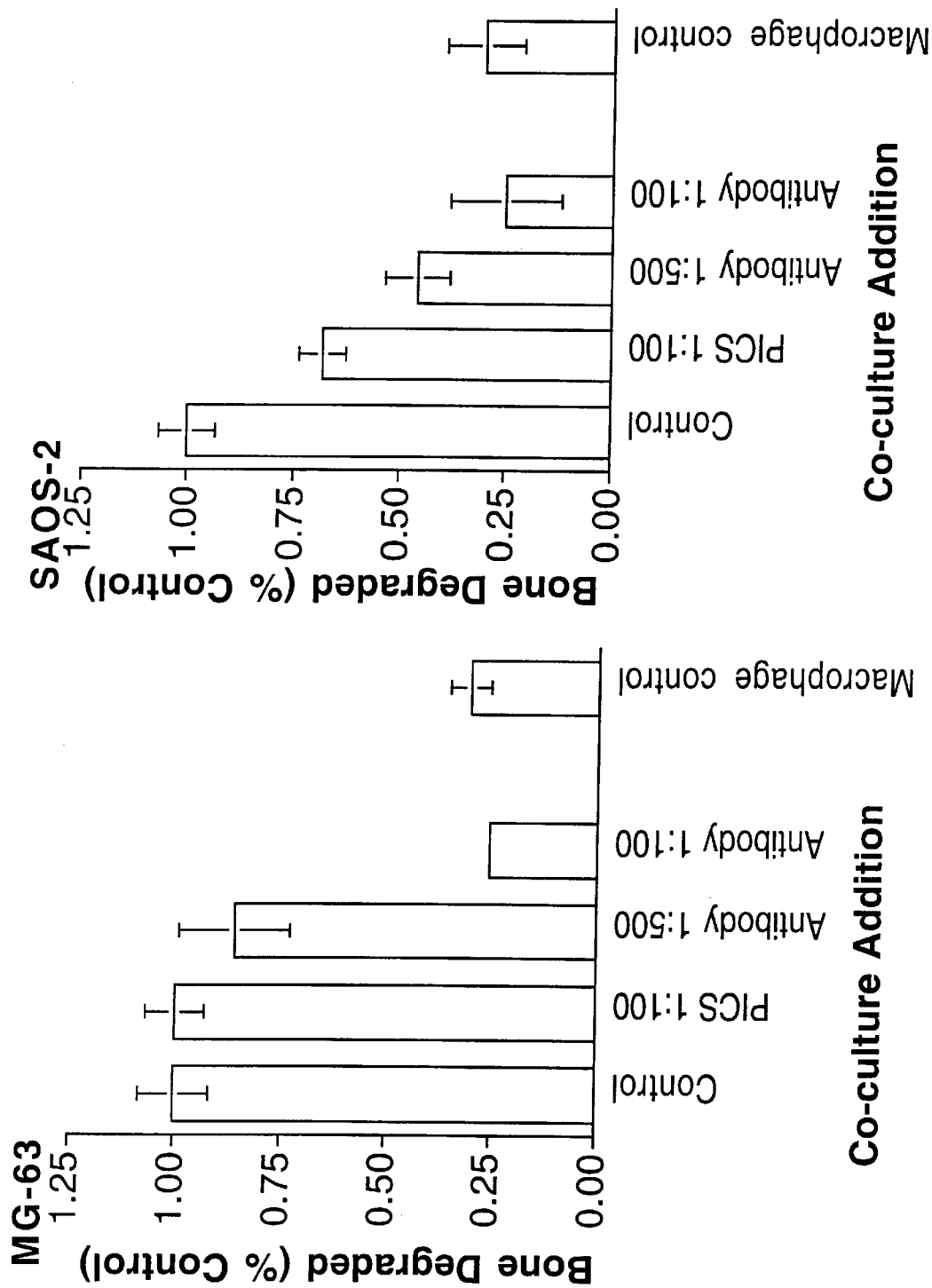
FIG. 3F shows the degradation of bone by osteoclasts formed in 14 day co-cultures of human macrophages and MG63 or SaOS2 cells, and effect of antibody to stem cell factor, assayed using 20 $\mu$g of $^3$H labeled substrate, measuring label released into the supernatant.[21]

The effects of a blocking antibody were further characterized by measuring TRAP and degradation of labeled bone substrate by osteoclasts formed. Consistent antibody dose dependent complete inhibition of the osteoclast-specific enzyme (TRAP) or bone degradation were noted, with similar results in co-cultures using parathyroid hormone-responsive (SaOS2) or unresponsive (MG63) osteoblast-like support cells (FIGS. 3E–3F). Pre-immune serum had no effect, and there was no effect on supporting cell density or appearance. Although bone regeneration is complex and involves many control mechanisms, the blocking data as shown in FIG. 3 suggests that controlled expression of cell-surface stem cell factor is central to matching bone synthesis and degradation.

EXAMPLE 9
Antisense Oligonucleotide Inhibition of SCF Expression

Figure 3G:
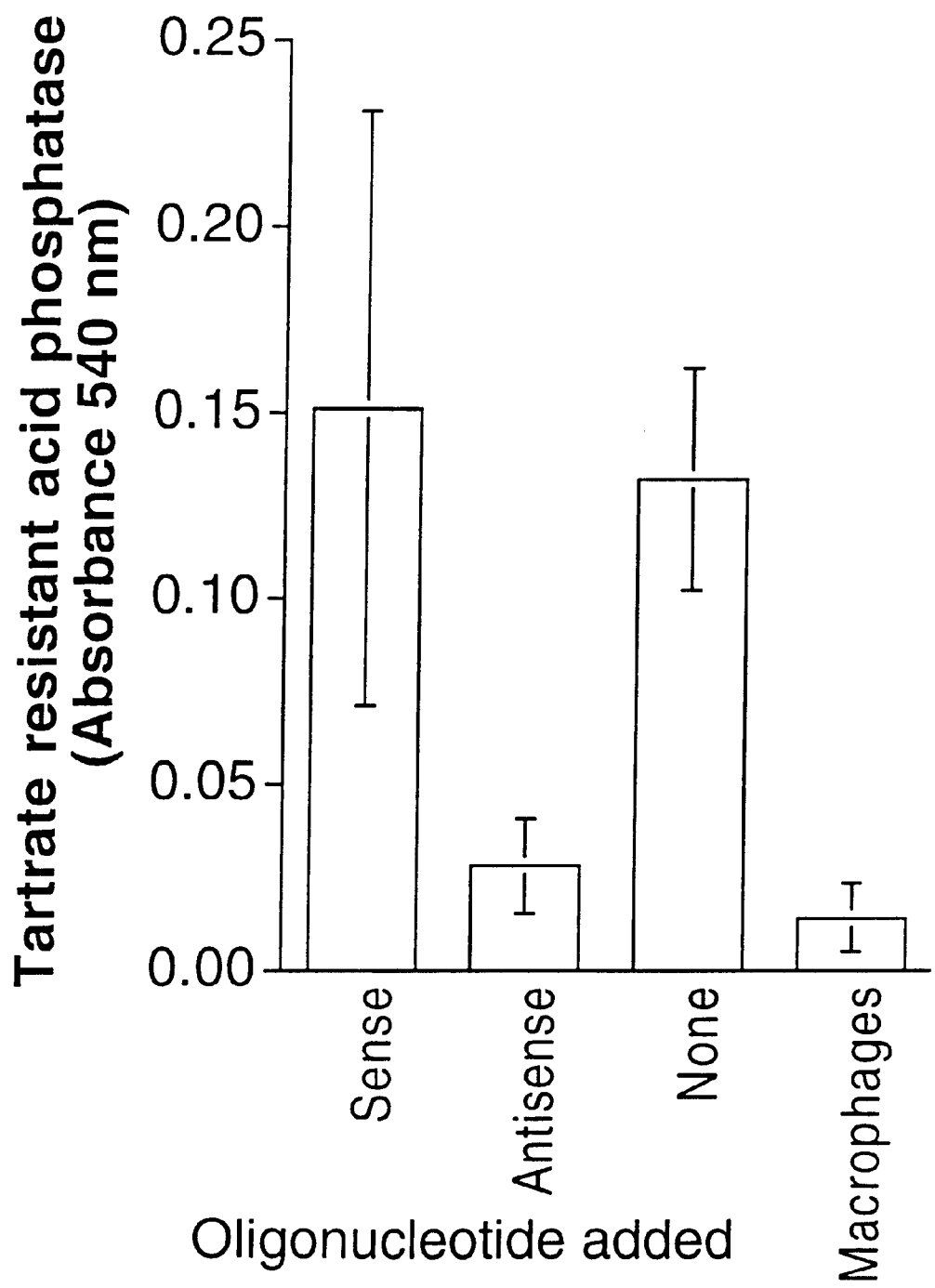
FIGS. 3G and 3H shows the effect of stem cell factor antisense phosphorothioate oligo-nucleotide and sense control on formation of TRAP and bone degradation, using MG63 cells with human macrophages and 1.5 $\mu$M sense or antisense oligonucleotides as indicated.
Figure 3H:
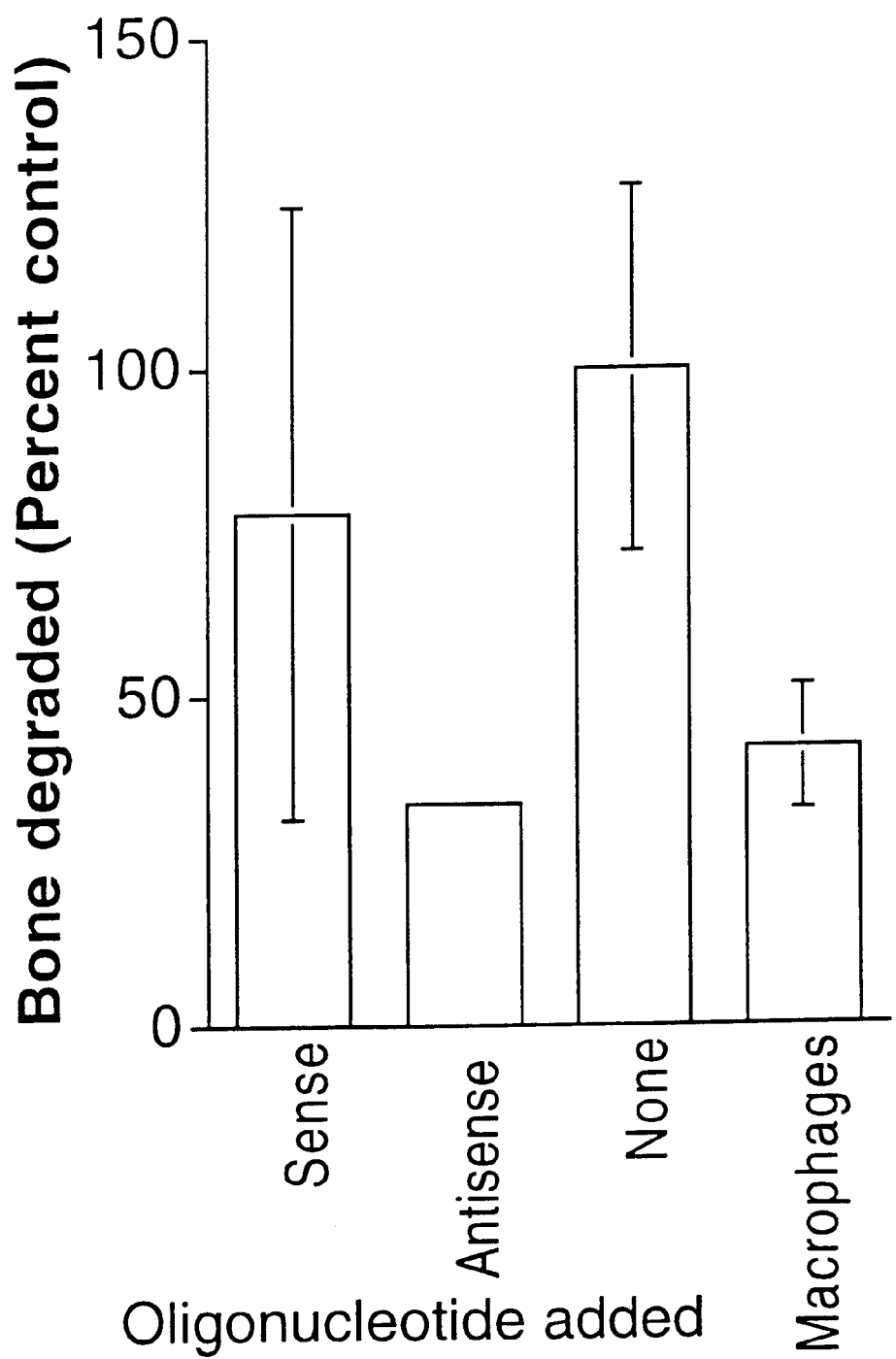

Antisense oligonucleotides were used as an independent method to reduce stem cell factor expression. Antisense or sense (control) phosphorothioate oligonucleotides centered on the stem-cell factor transcription start site were added to co-cultures of osteoclast precursors and supporting cells. Media were replaced, including oligonucleotides, every two days. The antisense oligonucleotide reduced osteoclast activity or TRAP production 20–40% at 0.5 µM and nearly totally at 1.5 –M (FIGS. 3G–3H). These results indicate that stem cell factor produced by osteoblasts is required for terminal differentiation of the osteoclast. As an additional control, oligonucleotide binding to the stem cell factor translation start site was confirmed by use of the antisense sequence for PCR amplification of SCF cDNA.

Figure 6A:
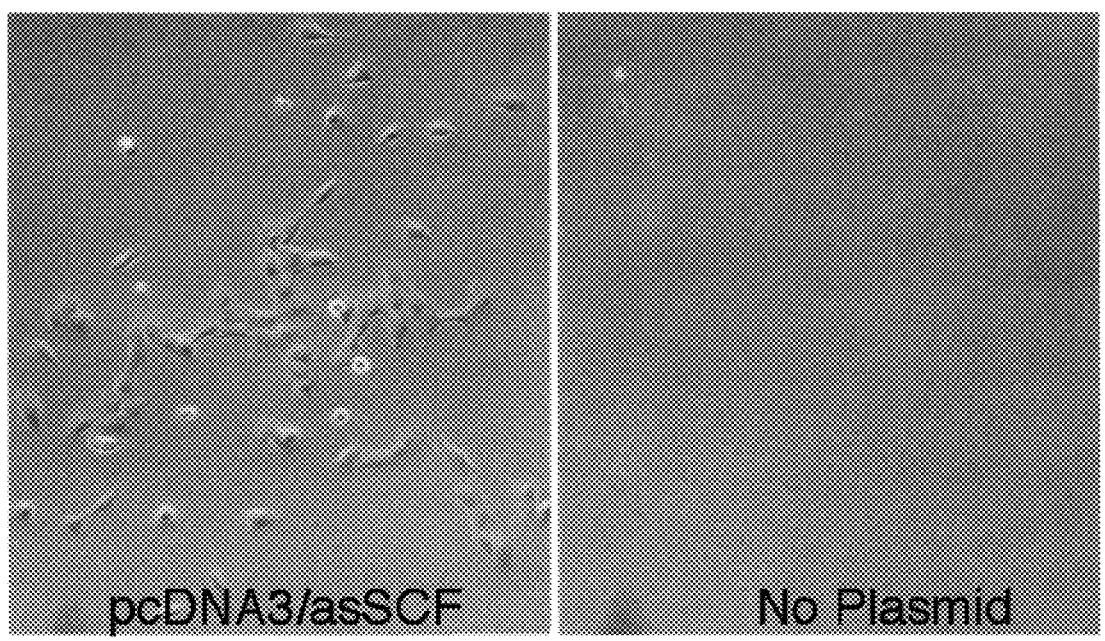
FIG. 6A shows the transfected MG63 cells growing in the neomycin analog G418. Transfected cells at this point had colonies (left panel), while the controls with empty vector had no living cells (right panel).
Figure 6B:
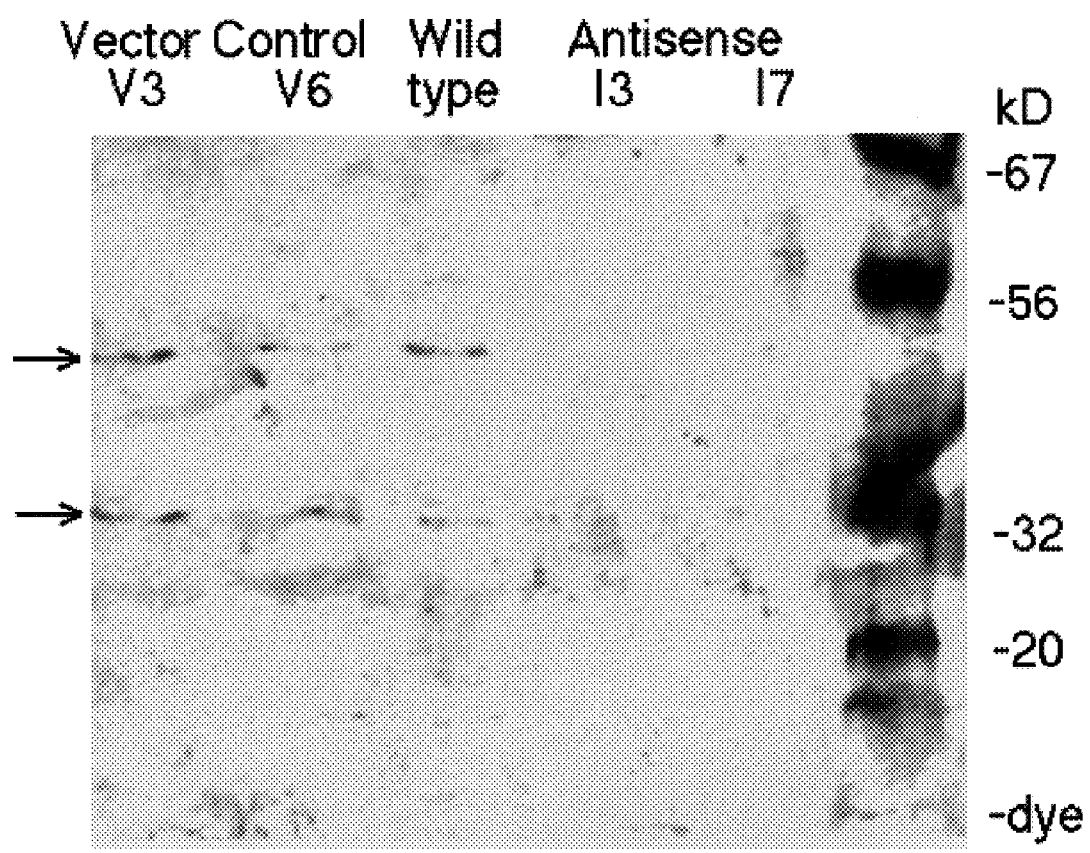
FIG. 6B is a Western analysis showing expression of the ~36 and 50 kDa forms of stem cell factor in MG63 with vector only (vector controls V3, V6) and wild type MG63 (middle lane), but not in transfectants expressing stem cell factor antisense (Antisense 13, 17).
Figure 8:
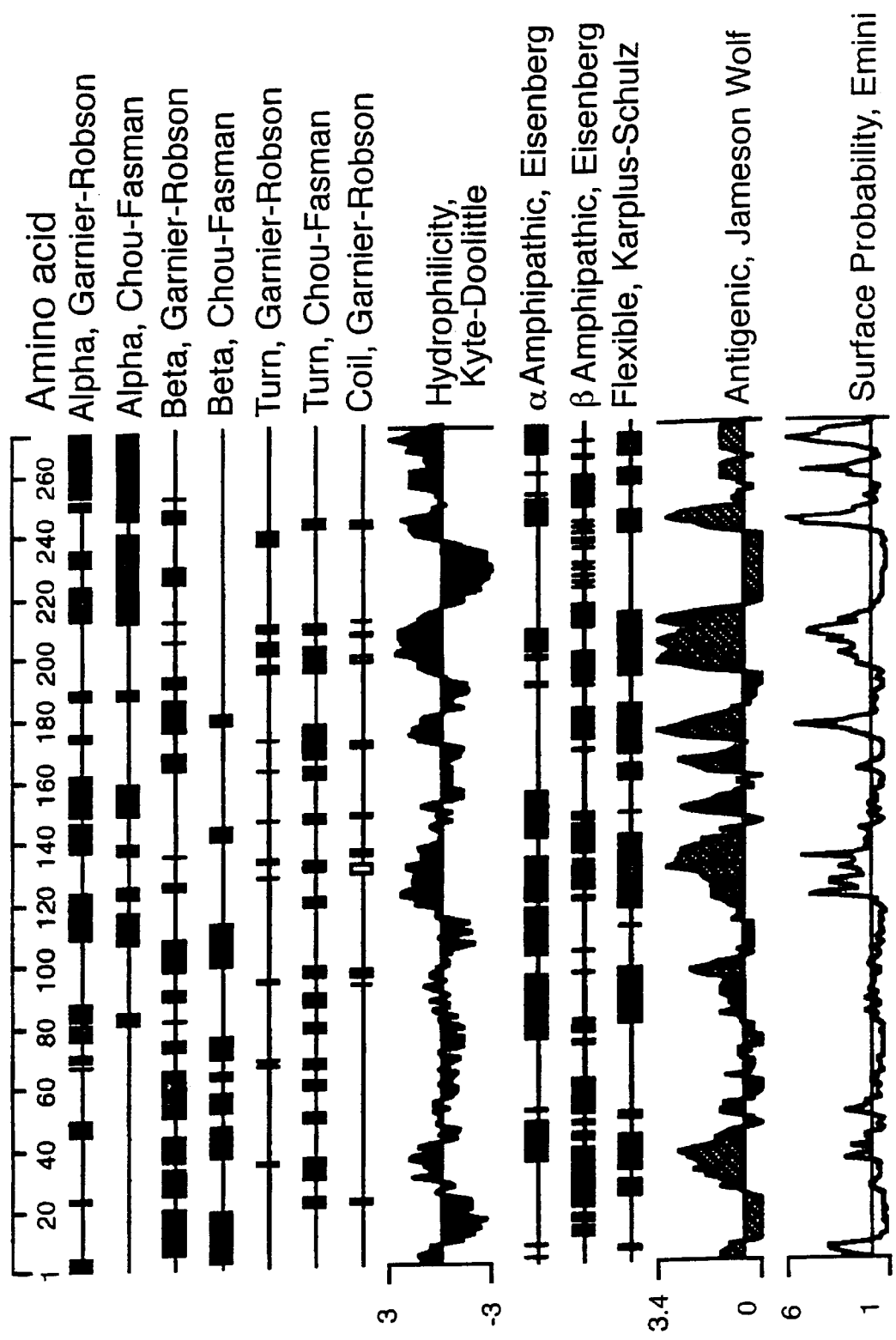
FIG. 8 shows analysis of the human stem cell factor protein, with the region used for antibody development highlighted. The region selected is conserved absolutely in mammals (E/Q and E/D substitutions in first three amino acids in lower species).

EXAMPLE 10
Elimination of Target Expression in MG63 Cells by Stable Transfection The oligonucleotide technique suffers from a number of limitations, including incomplete inhibition and toxicity. A more definitive approach is to transfect MG63 cells with plasmids to produce cells with varying expression of membrane stem cell factor. Plasmids were constructed that express stem cell factor sense and antisense RNA, MG63 cells were stably transfected with these and Western analysis was performed to demonstrate variable stem cell factor levels in the resultant cell lines (FIG. 6B). Assays of osteoclasts formed in co-cultures with stem cell factor-positive and stem cell factor-negative cells yielded results similar to those seen in FIG. 3G and 3H.

MG63 cells were stably transfected with pcDNA3 containing antisense to the translation start site of human c-fms ligand driven by the CMV promoter. A 633 base pair (bp) partial c-fms ligand cDNA was placed in the eukaryotic expression vector pCDNA3 (Invitrogen, San Diego, Calif.) in antisense orientation at Eco RI and Xba I sites; this construct was confirmed by sequencing. Vector elements included the enhancer-promoter for the immediate early gene of CMV as well as polyadenylation/transcription termination sites to improve RNA stability, neomycin resistance for selection in eukaryotes and SV40 ori for episomal replication. Empty vector and vector with antisense stem cell factor were transfected by the cationic lipid method (Tfx 20, Promega, Madison, Wis.) with 0.5 µg vector and 3:1 charge excess of cationic lipid. Incubation with 60% confluent MG63 cells at 37° C. for one hour followed, then selection in 100 µg/ml G418 (a neomycin) was carried out for ten days.

THE FOLLOWING REFERENCES WERE CITED HEREIN

1. Scheven, B. A., Visser, J. W. & Nijweide, P. J. In vitro osteoclast generation from different bone marrow fractions, including a highly enriched haematopoietic stem cell population. Nature. 321, 79–81, 1986.

2. Fujikawa, Y., Quinn, J. M, Sabokbar, A., McGee, J. O. & Athanasou, N. A. The human osteoclast precursor circulates in the monocyte fraction. Endocrinol. 137, 4058–60 (1996).

3. Rickard, D. J., Kassem, M., Hefferan, T. E., Sarkar, G., Spelsberg, T. C. & Riggs, B. L. Isolation and characterization of osteoblast precursor cells from human bone marrow. J. Bone Mineral Res. 11, 312–24, (1996).

4. Jimi, E., Nakamura, I., Amano, H., Taguchi, Y., Tsurukai, T., Tamura, M., Takahashi, N. & Suda, T. Osteoclast function is activated by osteoblastic cells through a mechanism involving cell-to-cell contact. Endocrinol. 137, 2187–90 (1996).

5. Rockoff, S. D. & Armstrong, J. D. Parathyroid hormone as a stimulus to mast cell accumulation in bone. Calcified Tissue Res. 5, 49–55 (1970).

6. Grabbe, J., Welker, P., Dippel, E., Czarnetzki, B. M. Stem cell factor, a novel cutaneous growth factor for mast cells and melanocytes. Arch Dermatol Res 28, 78–84 (1994).

7. Matsui, Y., Zsebo, K. M. & Hogan, B. L. Embryonic expression of a haematopoietic growth factor encoded by the S1 locus and the ligand for c-kit. Nature 347, 667–9 (1990).

8. Martin, F. H., Suggs, S. V., Langley, K. E., Lu, H. S., Ting, J., Okino, K. H., Morris, C. F., McNiece, I. K., Jacobsen, F. W., Mendiaz, E. A., Birkett, N. C., Smith, K. A., Johnson, M. J., Parker, V. P., Flores, J. C., Patel, C. J., Wypych, J., Sachder, R K., Pope, J. A., Leslie, J., Wen, D., Lin, C-H., Cupples, R. L., Zsebo, K. M. Primary structure and functional expression of rat and human stem cell factor DNAs. Cell 63, 203–11 (1990).

9. Gattei V, Aldinucci D, Quinn J M, Degan M, Cozzi M, Perin V, Iuliis A D, Juzbasic S, Improta S, Athanasou N A, Ashman L K, Pinto A. Human osteoclasts and preosteoclast cells (FLG 29.1) express functional c-kit receptors and interact with osteoblast and stromal cells via membrane-bound stem cell factor. Cell Growth & Differentiation. 7, 753–63 (1996).

10. Van 'T Hof, R J, Von Lindern, M, Nijweide, P J, and Beug, H. Stem cell factor stimulates chicken osteoclast activity in vitro. FASEB J 11, 287–93 (1997).

11. Ebi, Y., Kanakura, Y., Jippo-Kanemoto, T., Tsujimura, T., Furitsu, T., Ikeda, H., Adachi, S., Kasugai, T., Nomura, S., Kanayama, Y., Yamatadani, A., Shin-ichi, N., Matsuzawa, Y. & Kitamura, Y. Low c-kit expression of cultured mast cells of mi/mi genotype may be involved in their defective responses to fibroblasts that express the ligand for c-kit. Blood 80, 1454–62 (1992).

12. Suda, T., Nakamura, I., Jimi, E. & Takahashi, N. Regulation of osteoclast function. J. Bone Mineral Res. 12, 869–79 (1997).

13. Manolagas, S. C. & Jilka, R. L. Bone marrow, cytokines, and bone remodeling. Emerging insights into the pathophysiology of osteoporosis. New Engl J Med 332, 305–11 (1995).

14. Grano, M., Galimi, F., Zambonin, G., Colucci, S., Cottone, E., Zallone, A. Z., Comoglio, P. M. Hepatocyte growth factor is a coupling factor for osteoclasts and osteoblasts in vitro. Proc. Nat. Acad. Sci. U.S.A 93, 7644–8 (1996).

15. Grigoriadis, A. E., Wang, Z. Q., Cecchini, M. G., Hofstetter, W., Felix, R., Fleisch, H. A. & Wagner E. F. c-Fos: a key regulator of osteoclast-macrophage lineage determination and bone remodeling. Science 266, 443–8 (1994).

16. Hayase, Y., Muguruma, Y., Lee, M. Y. Osteoclast development from hematopoietic stem cells: apparent divergence of the osteoclast lineage prior to macrophage commitment. Exp. Hematol. 25, 19–25 (1997).

17. Martin, T. J., Ng, K. W. Mechanisms by which cells of the osteoblast lineage control osteoclast formation and activity. J. Cellular Biochem. 56, 357–66 (1994).

18. Li, C. F., Ross, F. P., Cao, X., Teitelbaum, S. L. Estrogen enhances $\alpha_v\beta_3$ integrin expression by avian osteoclast precursors via stabilization of $\beta_3$ integrin mRNA. Molecular Endocrinol. 9, 805–13 (1995).

19. Alvarez, et al., Generation of avian cells with the osteoclast phenotype from mononuclear phagocytes. Endocrinol. 128, 2324–35 (1991).

20. Vilamitjana-Amedee, J., Bareille, R., Rouais, F., Caplan, A. I., Harmand, M. F. Human bone marrow stromal cells express an osteoblastic phenotype in culture. In Vitro Cell Dev. Biol. 29A, 699–707 (1993).

21. Williams, J. P., Blair, H. C., McKenna, M. A., Jordan, S. E., McDonald, J. M. Regulation of Avian Osteoclastic $H^+$-ATPase and Bone Resorption by Tamoxifen and Calmodulin Antagonists. J. Biol. Chem. 271, 12488–95 (1996).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A non-naturally occurring non-human antibody inhibitor of osteoblastic stem cell factor that binds to EEDNEISMLQ (SEQ ID NO: 1) in the extracellular domain of the membrane associated form of osteoblastic stem cell factor, wherein said antibody inhibits the binding of osteoblastic stem cell factor to its receptor and inhibits differentiation of osteoclast induced by osteoblastic stem cell factor.

2. A composition comprising the antibody of claim 1 and a pharmaceutically acceptable carrier.

3. A method of inhibiting differentiation of osteoclasts induced by osteoblastic stem cell factor, comprising the step of:

administering a non-naturally occurring non-human antibody inhibitor of osteoblastic stem cell factor that binds to EEDNEISMLQ (SFQ ID NO: 1) in the extracellular domain of the membrane associated form of osteoblastic stem cell factor, wherein said antibody inhibitor inhibits the binding of osteoblastic stem cell factor to its receptor, thereby inhibiting differentiation of osteoclasts induced by osteoblastic stem cell factor.

* * * * *